US010085616B2

United States Patent
Takemoto et al.

(10) Patent No.: US 10,085,616 B2
(45) Date of Patent: Oct. 2, 2018

(54) ENDOSCOPE SYSTEM CONFIGURED TO PREVENT MIS-INSERTION OF TREATMENT TOOL IN CHANNEL AND METHOD OF OPERATING THE SAME

(71) Applicant: OLYMPUS CORPORATION, Tokyo (JP)

(72) Inventors: Shotaro Takemoto, Tokyo (JP); Kazuo Banju, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/361,971

(22) Filed: Nov. 28, 2016

(65) Prior Publication Data

US 2017/0071450 A1    Mar. 16, 2017

Related U.S. Application Data

(63) Continuation of application No. PCT/JP2015/066489, filed on Jun. 8, 2015.

(30) Foreign Application Priority Data

Sep. 5, 2014    (JP) .................................. 2014-181012

(51) Int. Cl.
  *A61B 1/018*    (2006.01)
  *A61B 1/00*    (2006.01)
  (Continued)

(52) U.S. Cl.
  CPC ........ *A61B 1/00055* (2013.01); *A61B 1/0016* (2013.01); *A61B 1/0052* (2013.01);
  (Continued)

(58) Field of Classification Search
  CPC . A61B 1/00055; A61B 1/00133; A61B 1/018; A61B 1/05; A61B 1/00087; A61B 1/00098; A61B 2017/0034
  See application file for complete search history.

(56) References Cited

U.S. PATENT DOCUMENTS 6,352,503 B1 *    3/2002    Matsui ............... A61B 1/00071
                                                        600/104
2006/0189845 A1 *    8/2006    Maahs ................. A61B 1/0008
                                                        600/146

(Continued)

FOREIGN PATENT DOCUMENTS

EP    2 052 671 A2    4/2009
EP    2 108 327 A1    10/2009

(Continued)

OTHER PUBLICATIONS

International Search Report dated Aug. 25, 2015 issued in PCT/JP2015/066489.

(Continued)

*Primary Examiner* — John P Leubecker
(74) *Attorney, Agent, or Firm* — Scully, Scott, Murphy & Presser, P.C.

(57) ABSTRACT

An endoscope system includes: an insertion part inserted into a body; an observation part provided at the insertion part and observing an inside of a viewing range defined in the front thereof; an arm part manipulated to be bent, a proximal end portion of which is provided at the insertion part, and which has an opening of a channel, through which a treatment tool is inserted, provided at a distal end side thereof; a first detection part detecting an out-of-viewing-range state where a center axis line in the opening of the channel does not pass through the viewing range; a second detection part detecting that the treatment tool has been inserted through the channel; and an alert part alerting a user when the second (Continued)

detection part detects that the treatment tool has been inserted through the channel and the first detection part detects the out-of-viewing-range state.

8 Claims, 9 Drawing Sheets

(51) Int. Cl.
*A61B 1/05* (2006.01)
*A61B 1/005* (2006.01)

(52) U.S. Cl.
CPC ........ *A61B 1/0055* (2013.01); *A61B 1/00098* (2013.01); *A61B 1/00133* (2013.01); *A61B 1/018* (2013.01); *A61B 1/05* (2013.01)

(56) References Cited

U.S. PATENT DOCUMENTS

| | | | | |
|---|---|---|---|---|
| 2007/0265502 | A1* | 11/2007 | Minosawa | A61B 1/00177 600/173 |
| 2009/0198104 | A1* | 8/2009 | Sugiyama | A61B 1/00039 600/146 |
| 2009/0209809 | A1* | 8/2009 | Schaller | A61B 1/018 600/103 |
| 2009/0318797 | A1* | 12/2009 | Hadani | A61B 1/00082 600/424 |
| 2009/0326318 | A1* | 12/2009 | Tognaccini | A61B 1/00183 600/104 |
| 2010/0016659 | A1* | 1/2010 | Weitzner | A61B 1/00073 600/104 |
| 2010/0152538 | A1* | 6/2010 | Gleason | A61B 1/00055 600/117 |
| 2010/0217072 | A1 | 8/2010 | Kondoh et al. | |
| 2010/0274087 | A1 | 10/2010 | Diolaiti et al. | |
| 2011/0040305 | A1* | 2/2011 | Gomez | A61B 19/2203 606/130 |
| 2011/0071508 | A1* | 3/2011 | Duval | A61B 1/00087 606/1 |
| 2012/0016191 | A1* | 1/2012 | Ito | A61B 1/00087 600/104 |
| 2012/0182409 | A1* | 7/2012 | Moriyama | A61B 1/00006 348/65 |
| 2012/0265007 | A1* | 10/2012 | Moriyama | A61B 1/0055 600/104 |
| 2013/0072753 | A1* | 3/2013 | Zappia | A61B 1/0008 600/108 |
| 2017/0165013 | A1* | 6/2017 | Itkowitz | A61B 34/35 |

FOREIGN PATENT DOCUMENTS

| | | |
|---|---|---|
| EP | 2532299 A1 | 12/2012 |
| JP | 2007-029232 A | 2/2007 |
| JP | 2007-259998 A | 10/2007 |
| JP | 2008-536552 A | 9/2008 |
| JP | 2010-057914 A | 3/2010 |
| WO | WO 2006/110275 A2 | 10/2006 |
| WO | WO 2012/035923 A1 | 3/2012 |

OTHER PUBLICATIONS

Japanese Office Action dated Apr. 5, 2016 issued in Japanese Application No. 2015-561780.
Extended Supplementary European Search Report dated May 22, 2018 in European Patent Application No. 15 83 8394.3.

* cited by examiner

ENDOSCOPE SYSTEM CONFIGURED TO PREVENT MIS-INSERTION OF TREATMENT TOOL IN CHANNEL AND METHOD OF OPERATING THE SAME

This application is a continuation application based on PCT Patent Application No. PCT/JP2015/066489, filed Jun. 8, 2015, whose priority is claimed on Japanese Patent Application No. 2014-181012, filed Sep. 5, 2014. The contents of both the PCT Patent Application and the Japanese Patent Application are incorporated herein by reference.

BACKGROUND OF THE INVENTION

Field of the Invention

The present invention relates to an endoscope system which is inserted into and used in a body and a method of operating the endoscope system.

Description of Related Art

In the related art, as an example of minimally invasive treatment, a procedure in which an endoscope system such as a laparoscope is inserted into a body and a gallbladder or the like is removed is performed. A system disclosed in Japanese Unexamined Patent Application, First Publication No. 2010-057914 is known as this type of endoscope system.

An endoscope system disclosed in Japanese Unexamined Patent Application, First Publication No. 2010-057914 is configured such that two treatment tools are inserted into a manipulator. The manipulator includes an insertion part which is inserted into a body, a distal end portion which is attached to a distal end of the insertion part, and a manipulation part which is attached to a proximal end side of the insertion part.

The insertion part is a rigid tubular member which does not have flexibility. Two channels are provided inside the insertion part. An observation part (an observation device) is attached to the distal end of the insertion part.

The distal end portion is for the purpose of performing various procedures on tissue inside a body cavity, and includes a first arm (an arm part), a second arm (an arm part), and a link part configured to space a distal end side of the first arm apart from a distal end side of the second arm to set the first arm and the second arm in a positional relationship in which a procedure is easily performed. That is to say, both arms and the observation part are attached to the distal end of the insertion part.

Each of the arms is provided with a bending part which is configured by a plurality of joint rings that are connected to each other such that the plurality of joint rings are arranged side by side in an axis line direction. Each of the bending parts is connected to a manipulation part by a transfer member which is constituted by a wire and a rod. The bending parts can be bent by manipulating the manipulation part. Channels of the arms are in communication with a channel of the insertion part.

When the endoscope system configured as described above is used, a hole in communication with a body cavity in an abdominal wall, a chest wall, or the like is opened, and a trocar is inserted into the hole. The manipulator is inserted into the trocar and is inserted into the body cavity. A treatment tool is inserted into the channel from a proximal end of the manipulation part, and the arms are opened by manipulating the manipulation part in a shape in which a procedure is easily performed. Then, both arms are moved in a desired direction by manipulating the manipulation part upward, downward, leftward, or rightward while grasping a manipulation part of the treatment tool, and various procedures are performed using a treatment part of a distal end of the treatment tool.

SUMMARY OF THE INVENTION

According to a first aspect of the present invention, an endoscope system includes: an insertion part capable of being inserted into a body; an observation part provided at the insertion part, the observation part being capable of observing an inside of a viewing range defined in a front of the observation part; an arm part capable of being manipulated to be bent, a proximal end portion of the arm part being provided at the insertion part, the arm part having an opening of a channel, through which a treatment tool is capable of being inserted, provided at a distal end side of the arm part; a first detection part that detects an out-of-viewing-range state in which a center axis line in the opening of the channel does not pass through the viewing range of the observation part; a second detection part that detects that the treatment tool has been inserted through the channel; and an alert part that alerts a user when the second detection part detects that the treatment tool has been inserted through the channel and the first detection part detects the out-of-viewing-range state.

According to a second aspect of the present invention, the endoscope system according to the first aspect may further include: a blockade part that deforms at least a portion of the channel such that the treatment tool is incapable of being inserted through the channel if the first detection part detects the out-of-viewing range state when the second detection part detects that the treatment tool has been inserted through the channel.

According to a third aspect of the present invention, the endoscope system according to the first aspect may further include: a visual field movement unit that moves the observation part such that the center axis line in the opening of the channel passes through the viewing range if the first detection part detects the out-of-viewing-range state when the second detection part detects that the treatment tool has been inserted through the channel.

According to a fourth aspect of the present invention, in the endoscope system according to the first aspect, the alert part may display an alert or generate a sound.

According to a fifth aspect of the present invention, a method of operating an endoscope system, which includes an insertion part capable of being inserted into a body, an observation part provided at the insertion part, the observation part being capable of observing an inside of a viewing range defined in a front of the observation part, and an arm part capable of being manipulated to be bent, a proximal end portion of the arm part being provided at the insertion part, the arm part having an opening of a channel, through which a treatment tool is capable of being inserted, provided at a distal end side of the arm part, includes: detecting an out-of-viewing-range state in which a center axis line in the opening of the channel does not pass through the viewing range of the observation part; detecting that the treatment tool has been inserted through the channel; and alerting a user when that the treatment tool has been inserted through the channel is detected and the out-of-viewing-range state is detected.

DETAILED DESCRIPTION OF THE INVENTION

First Embodiment

Hereinafter, a first embodiment of an endoscope system according to the present invention will be described with reference to FIGS. 1 to 5.

Figure 1:
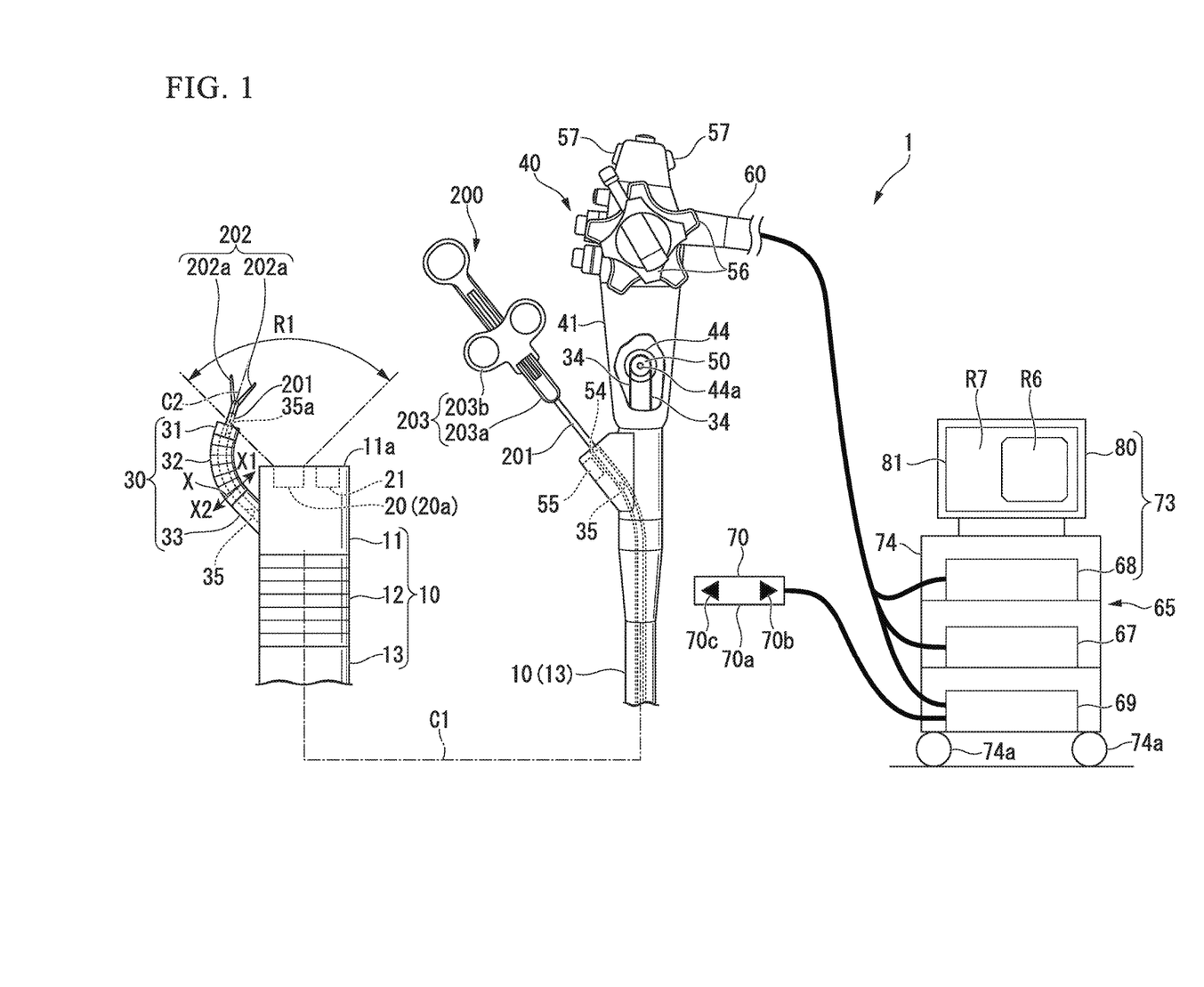
FIG. 1 is an overall view showing a partly cut endoscope system according to a first embodiment of the present invention.
Figure 2:
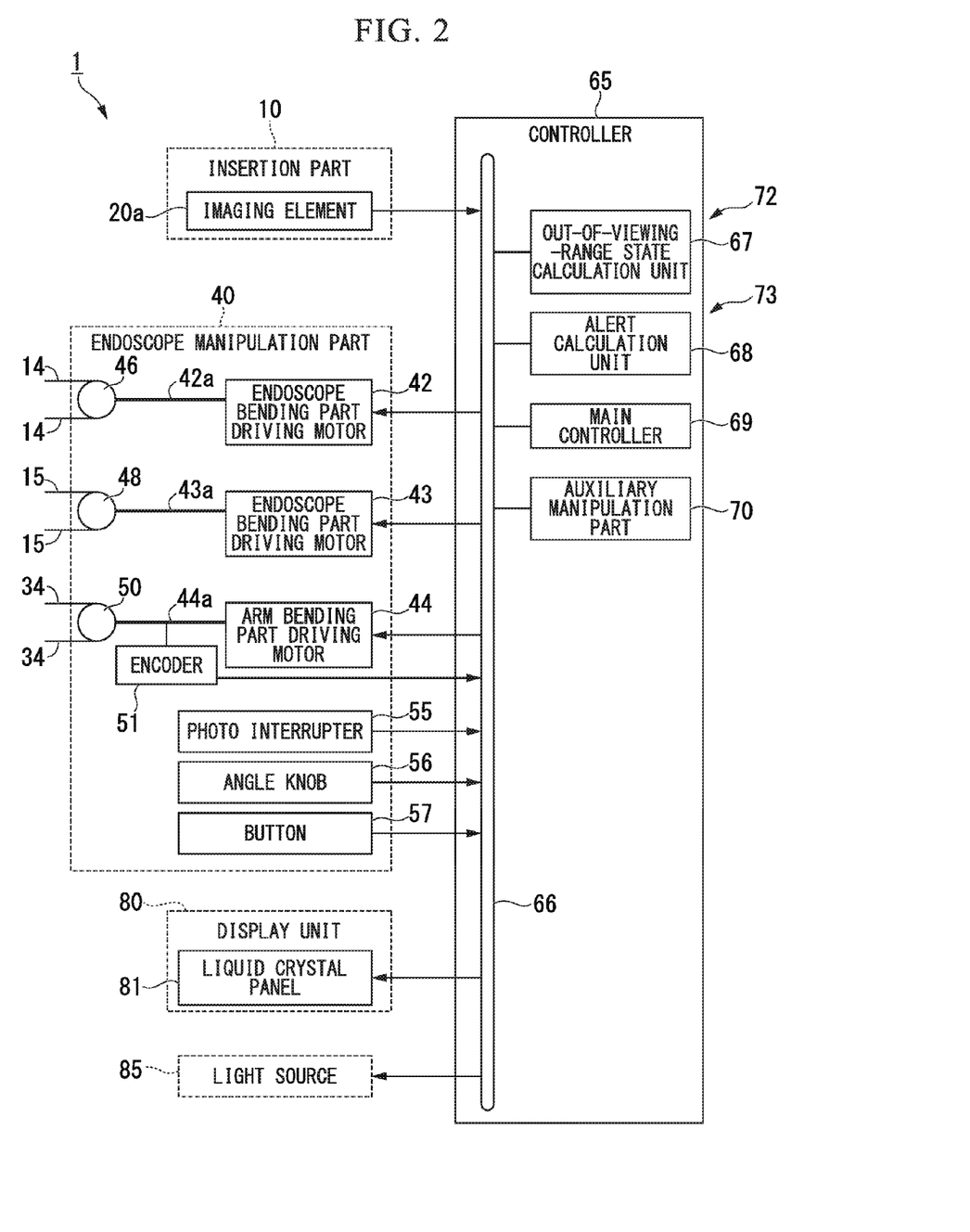
FIG. 2 is a block diagram of the endoscope system.

As shown in FIGS. 1 and 2, an endoscope system 1 according to this embodiment is used together with a treatment tool 200. First, the treatment tool 200 will be described below.

The treatment tool 200 is not particularly limited as long as a treatment tool insertion part 201 has flexibility. For example, in the treatment tool 200 according to this embodiment, a grasping part (a treatment part) 202 having a pair of grasping pieces 202a is attached to a distal end portion of the treatment tool insertion part 201, and a treatment to manipulation part 203 configured to manipulate the grasping part 202 is attached to a proximal end portion of the treatment tool insertion part 201.

A treatment tool manipulation wire (not shown) is inserted through a conduit line of the treatment tool insertion part 201 such that the treatment tool manipulation wire can be advanced or retracted with respect to the treatment tool insertion part 201. A distal end portion of the treatment tool manipulation wire is connected to the pair of grasping pieces 202a via a link mechanism (not shown). The link mechanism is configured to be able to perform an opening and closing manipulation in which distal end portions of the pair of grasping pieces 202a are spaced apart from or approach each other.

The pair of grasping pieces 202a and the link mechanism are formed of a metal such as stainless steel or titanium.

The treatment tool manipulation part 203 has a manipulation part main body 203a which is attached to the treatment tool insertion part 201 and a slider 203b which is slidably attached to the manipulation part main body 203a in a longitudinal direction of the treatment tool insertion part 201. A proximal end portion of the treatment tool manipulation wire is attached to the slider 203b.

In the treatment tool 200 configured in this way, when the slider 203b slides with respect to the manipulation part main body 203a in the longitudinal direction, the treatment tool manipulation wire is advanced or retracted with respect to the treatment tool insertion part 201. Thus, the link mechanism manipulates the pair of grasping pieces 202a so that they can be opened or closed.

The endoscope system 1 includes a flexible insertion part 10 which can be inserted into a body, an observation unit (an observation part) 20 which is provided at a distal end surface 11a of the insertion part 10 in a state in inch the observation unit 20 is exposed, an arm part 30 which can be manipulated to be bent and a proximal end portion of which is attached to the insertion part 10, an endoscope manipulation part 40 which is attached to a proximal end portion of the insertion part 10, and a controller 65 and a display unit 80 which are connected to the endoscope manipulation part 40 via a universal cable 60.

In the following description, the insertion part 10 side with respect to the endoscope manipulation part 40 which will be described below and the endoscope manipulation part 40 side with respect to the insertion part 10 are referred to as a distal end side and a proximal end side, respectively.

The insertion part 10 has a rigid distal end part 11 which is provided at a distal end side, an endoscope bending part 12 which is provided at a proximal end side of the distal end rigid part 11 and can be manipulated to be bent by the endoscope manipulation part 40, and a flexible tube part 13 which is provided at a proximal end side of the endoscope bending part 12.

The distal end rigid part 11 is formed of a material which is relatively hard enough that a user such as an operator cannot bend the distal end rigid part 11 without using a tool. The distal end rigid part 11 can be formed of a metal such as, for example, stainless steel or titanium.

The observation unit 20 described above and a lighting unit 21 which irradiates the front thereof with illumination light are provided at the distal end surface 11a of the distal end rigid part 11.

The lighting unit 21 has an optical fiber (not shown). The lighting unit 21 irradiates the front of the lighting unit 21 with light which is incident on a proximal end portion of the optical fiber as illumination light.

The observation unit 20 has an imaging element 20a such as a group of lenses or a complementary metal oxide semiconductor (CMOS). An image of light which is incident on the group of lenses from the outside is formed on a light receiving surface on the imaging element 20a through the group of lenses. The imaging element 20a acquires an image of a figure which is formed on the light receiving surface. The imaging element 20a converts the acquired image into a signal and transmits the signal to the controller 65. The imaging element 20a of the observation unit 20 can observe an inside of a viewing range R1 defined in the front of the distal end surface 11a of the distal end rigid part 11. The viewing range R1 has, for example, a quadrangular pyramid shape.

A plurality of joint rings (not shown) which are arranged in a longitudinal direction of the insertion part 10 are provided in the endoscope bending part 12. The joint rings, which are adjacent to each other in the longitudinal direction, are rotatably coupled to each other by pins. Positions of the adjacent joint rings, which are coupled by the pins, are shifted around a center axis line C1 of the insertion part 10 for each of the joint rings, which are adjacent to each other in the longitudinal direction, at a predetermined angle.

Distal end portions of endoscope manipulation wires 14 and 15 (refer to FIG. 2) are attached to the joint ring that is closest to the distal end among the plurality of joint rings.

The four endoscope manipulation wires 14 and 15 are attached around the axis line C1 at equal angles. Each of the endoscope manipulation wires 14 and 15 extends to the endoscope manipulation part 40 via the plurality of joint rings and the flexible tube part 13. The endoscope manipulation wires 14 and 15 are advanced or retracted with respect to the flexible tube part 13 in the longitudinal direction of the insertion part 10 so that the endoscope bending part 12 can be bent with respect to the axis line C1 of the insertion part 10 in a desired direction.

The flexible tube part 13 is formed of a flexible resin or coil.

The arm part 30 has a rigid arm rigid part 31 which is provided at a distal end side, an arm bending part 32 which is provided at a proximal end side of the arm rigid part 31 and can be manipulated to be bent, and a rigid arm rigid part 33 which is provided at a proximal end side of the arm bending part 32.

The arm rigid parts 31 and 33 can be formed of the same material as the distal end rigid part 11.

The arm bending part 32 is configured in the same manner as the endoscope bending part 12. Distal end portions of two arm manipulation wires 34 are attached to a joint ring (not shown) which is disposed inside the arm bending part 32. The arm manipulation wires 34 extend to the endoscope manipulation part 40 through the plurality of joint rings, the arm rigid part 33, and the insertion part 10. A proximal end portion of the arm rigid part 33 is attached to a lateral surface of the distal end rigid part 11.

The arm part 30 is formed with a channel 35 through which the treatment tool 200 can be inserted. The channel 35 is formed as a conduit line of a channel tube (not shown). A resin with elasticity such as rubber or silicone is used for the channel tube, and the channel tube has flexibility. An opening 35a of a distal end side of the channel 35 is disposed in a distal end surface of the arm rigid part 31.

The arm manipulation wires 34 is advanced or retracted with respect to the arm rigid part 33 in a longitudinal direction of the arm part 30 so that the arm bending part 32 can be bent in a direction X which is perpendicular to the longitudinal direction of the arm part 30. The direction X is a direction in which the arm rigid part 31 approaches the viewing range R1 or is spaced apart from the viewing range R1.

When the arm bending part 32 has a straight shape, the arm part 30 also has a straight shape as a whole.

As shown in FIG. 2, endoscope bending part driving motors 42 and 43 and an arm bending part driving motor 44 are built in a manipulation part main body 41 of the endoscope manipulation part 40.

A pulley 46 is attached to a rotation shaft 42a of the endoscope bending part driving motor 42 coaxially with the rotation shaft 42a. Proximal end portions of the two endoscope manipulation wires 14 are each attached to the pulley 46.

The endoscope bending part driving motor 43 and the arm bending part driving motor 44 are configured in the sane manner as the endoscope bending part driving motor 42. That is to say, a pulley 48 is attached to a rotation shaft 43a of the endoscope bending part driving motor 43 coaxially with the rotation shaft 43a. Proximal end portions of the two endoscope manipulation wires 15 are each attached to the pulley 48.

A pulley 50 is attached to a rotation shaft 44a of the arm bending part driving motor 44 coaxially with the rotation shaft 44a. Proximal end portions of the two arm manipulation wires 34 are each attached to the pulley 50. In the arm bending part driving motor 44, an encoder 51 is connected to the rotation shaft 44a. The amount of rotation of the rotation shaft 44a and the direction in which the rotation shaft 44a is rotated, which are detected by the encoder 51, are transmitted to the controller 65.

When the arm bending part 32 has a straight shape, the rotation shaft 44a of the arm bending part driving motor 44 is at a reference position. When the rotation shaft 44a is rotated to a first side around the rotation shaft 44a from the reference position, as shown in FIG. 1, the arm bending part 32 is bent to a first side X1 of the direction X, in which the arm bending part 32 approaches the viewing range R1.

On the other hand, when the rotation shaft 44a is rotated to a second side around the rotation shaft 44a from the reference position, the arm bending part 32 is bent to a second side X2 of the direction X, in which the arm bending part 32 is spaced apart from the viewing range R1.

There is a constant correspondence between the direction and the amount of rotation in which the rotation shaft 44a is rotated from the reference position and a bending shape of the arm bending part 32. When the bending shape of the arm bending part 32 is determined, it is determined whether or not the arm bending part 32 is in an in-viewing-range state in which a center axis line C2 in the opening 35a of the channel 35 passes through the viewing range R1 of the observation unit 20. When the arm bending part 32 is in the in-viewing-range state, as the treatment tool 200 is inserted through the channel 35, the inserted treatment tool 200 passes through the viewing range R1. Thus, the treatment tool 200 which protrudes from the distal end of the channel 35 is observed by the observation unit 20, and the treatment tool 200 is displayed on the display unit 80.

Figure 3:
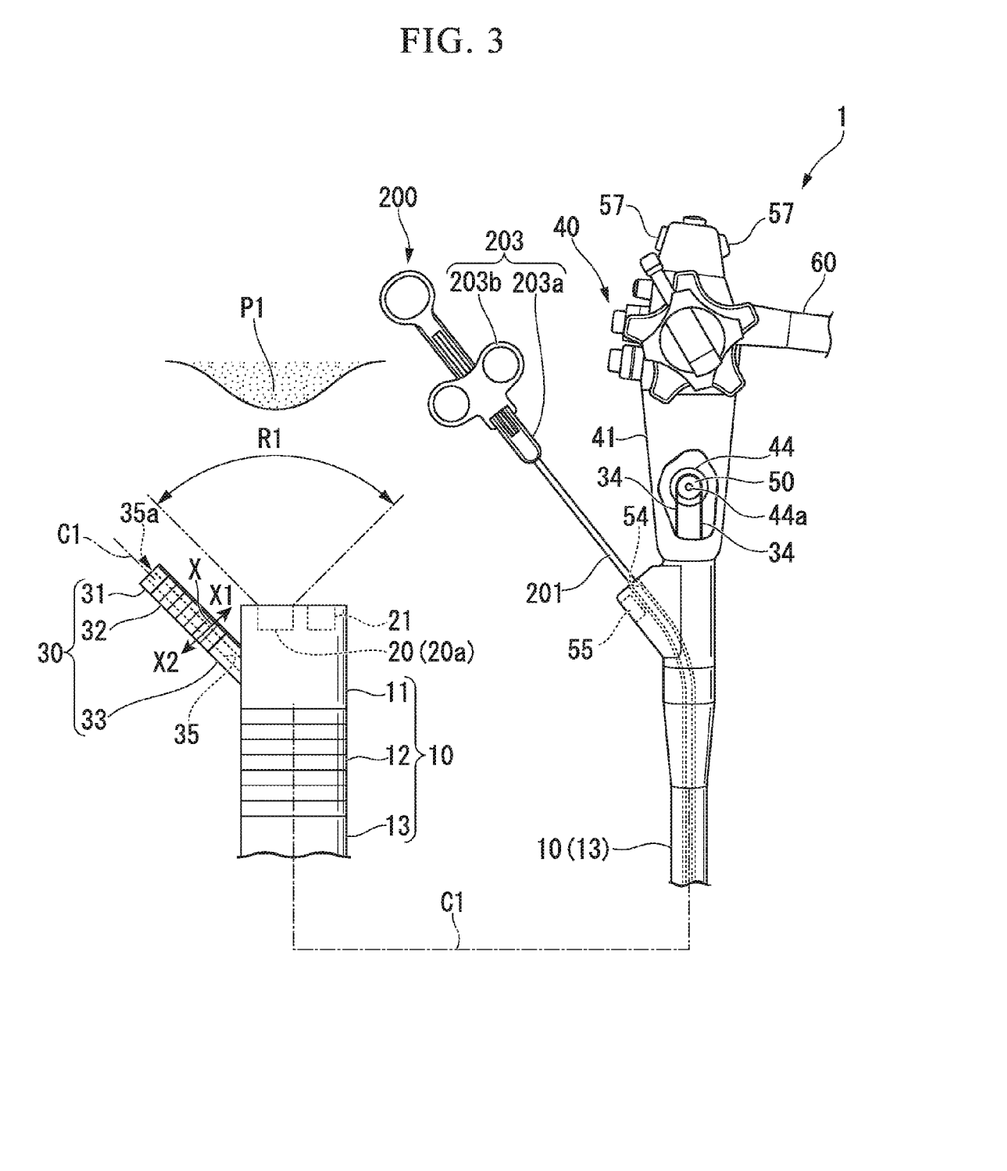
FIG. 3 is a view showing a procedure using the endoscope system.

On the other hand, as shown in FIG. 3, when the arm bending part 32 is in an out-of-viewing-range state in which the center axis line C2 of the channel 35 does not pass through the viewing range R1 of the observation unit 20, the treatment tool 200 which is inserted through the channel 35 does not pass through the viewing range R1. For this reason, even if the treatment tool 200 is inserted through the channel 35, the treatment tool 200 which protrudes from the distal end of the channel 35 cannot be observed by the observation unit 20.

As shown in FIG. 1, a forceps port 54 which is provided at the distal end side of the manipulation part main body 41 is in communication with a proximal end portion of the channel 35.

A photo interrupter (a second detection part) 55 which is shown in FIGS. 1 and 2 is attached to the proximal end port on of the channel 35. The photo interrupter 55 is a device having a well-known constitution in which a light emitting element and a light receiving element (which are not shown) are built. The light emitting element and the light receiving element are disposed to face each other such that the channel tube which forms the channel 35 is interposed therebetween. Under normal circumstances, the light receiving element can receive detection light which is emitted by the light emitting element. When the grasping part 202 and the treatment tool insertion part 201 of the treatment tool 200 which is inserted through the channel 35 block the detection light which is emitted by the light emitting element, the light receiving element cannot receive the detection light. Thus, the photo interrupter 55 detects that the treatment tool 200 has been inserted through the channel 35. The photo interrupter 55 transmits a detection result to the controller 65.

An angle knob 56 and a button 57 are attached to an outer surface of a proximal end side of the manipulation part main body 41.

The angle knob 56 is manipulated so that the endoscope bending part driving motors 42 and 43 are driven and the rotation shafts 42a and 43a are thus rotated. Thus, the endoscope manipulation wires 14 and 15 are advanced or retracted in the longitudinal direction of the insertion part 10, and the endoscope bending part 12 is bent.

The button 57 is manipulated so that light can be radiated from a light source 85 which will be described below.

The controller 65 has an out-of-viewing-range state calculation unit 67, an alert calculation unit 68, a main controller 69, and the auxiliary manipulation part 70 which are connected to a bus 66. Note that a first detection part 72 is constituted by the encoder 51 and the out-of-viewing-range state calculation unit 67, and an alert part 73 is constituted by the alert calculation unit 68 and the display unit 80.

The imaging element 20a of the insertion part 10, the endoscope bending part driving motors 42 and 43 of the endoscope manipulation part 40, the arm bending part driving motor 44, the encoder 51, the photo interrupter 55, the angle knob 56, the button 57, the display unit 80, and the light source 85 are connected to the bus 66.

The out-of-viewing-range state calculation unit 67, the alert calculation unit 68, and the main controller 69 are each constituted by a calculation element, a memory, a control program, and the like.

The direction and the amount of rotation in which the rotation shaft 44a of the arm bending part driving motor 44 is rotated from the reference position and a table which shows whether the arm bending part 32 at this time is in the in-viewing-range state or the out-of-viewing-range state described above are stored in the memory of the out-of-viewing-range state calculation unit 67 which constitutes the first detection part 72.

The calculation element of the out-of-viewing-range state calculation unit 67 detects whether the arm bending part 32 is in the in-viewing-range state or the out-of-viewing-range state on the basis of the amount of rotation of the rotation shaft 44a and the direction in which the rotation shaft 44a is rotated, which are transmitted from the encoder 51, and the table which is stored in the memory. The out-of-viewing-range state calculation unit 67 transmits a detection result to the alert calculation unit 68.

When the photo interrupter 55 detects that the treatment tool 200 has been inserted through the channel 35, the alert calculation unit 68 alerts the user by displaying an alert on the display unit 80 if the first detection part 72 detects the out-of-viewing-range state.

The main controller 69 performs various processes such that a signal which is transmitted from the imaging element 20a is appropriately displayed on the display unit 80. Also, the main controller 69 controls the light source 85 or the like on the basis of an instruction through the angle knob 56 or the button 57.

The out-of-viewing-range state calculation unit 67, the alert calculation unit 68, and the main controller 69 are disposed at a rack 74 having wheels 74a which are attached to a low portion thereof.

In the auxiliary manipulation part 70, bending manipulation buttons 70b and 70c are provided on a manipulation part main body 70a.

The bending manipulation buttons 70b and 70c of the auxiliary manipulation part 70 are manipulated so that the arm bending part driving motor 44 is driven and the rotation shaft 44a is thus rotated. Thus, the arm manipulation wires 34 are advanced or retracted in the longitudinal direction of the arm part 30, and the arm bending part 32 is bent to the first side X1 or the second side X2.

The display unit 80 has a liquid crystal panel 81. An image display region R6 which displays an image on the basis of a signal which is transmitted from the main controller 69 of the controller 65 and an information display region R7 which displays text or the like which indicates a date or an alert are provided in the liquid crystal panel 81.

The display unit 80 is attached to, for example, an upper portion of the rack 74.

The light source 85 irradiates the optical fiber of the insertion part 10 with light by being supplied with predetermined power.

Next, an action of the endoscope system 1 configured as described above will be described.

The user such as the operator inserts the insertion part 10 of the endoscope system 1 through, for example, an overtube (not shown), and the arm part 30 is covered with the overtube. The endoscope system 1 is activated, the button 57 is manipulated, and light is radiated from the light source 85. The light which is radiated from the light source 85 is guided to the optical fiber and illuminates a distal end side of the distal end surface 11a of the insertion part 10.

An image within the viewing range R1, which is acquired by the observation unit 20, is processed by the main controller 69 of the controller 65 and is displayed in the image display region R6 of the liquid crystal panel 81.

The user inserts the insertion part 10, which is covered with the overtube, through a mouth or the like of a patient while confirming an image which is displayed on the liquid crystal panel 81. At this time, the endoscope bending part 12 is inserted while being bent by manipulating the angle knob 56 as necessary.

As shown in FIG. 3, the insertion part 10 is inserted to a position at a distal end of the insertion part 10 faces a site to be treated P1. The overtube is moved to the proximal end side with respect to the insertion part 10, and the distal end rigid part 11 of the insertion part 10 and the arm part 30 protrude from a distal end of the overtube to the distal end side. Here, a case in which the arm part 30 has a straight shape as a whole will be described.

The out-of-viewing-range state calculation unit 67 of the first detection part 72 detects whether the arm part 30 is in the out-of-viewing-range state, and transmits a detection result to the alert calculation unit 68.

The user inserts the treatment tool 200 through the channel 35 of the endoscope system 1 from the grasping part 202 side. The photo interrupter 55 detects that the treatment tool 200 has been inserted through the channel 35, and transmits a detection result to the alert calculation unit 68 of the controller 65.

Figure 4:
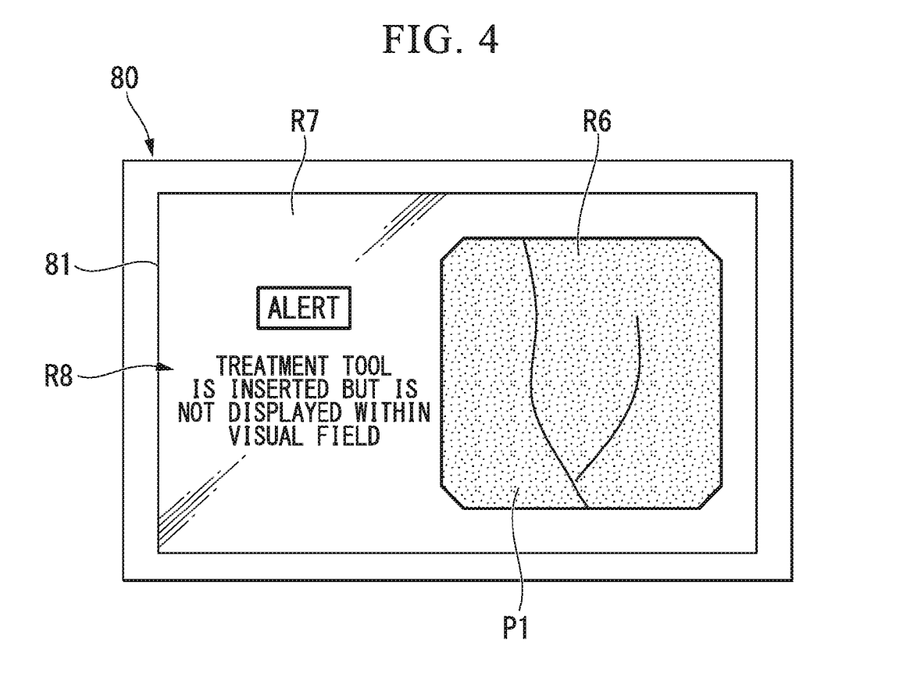
FIG. 4 is a view showing an example of an alert which is displayed on a display unit of the endoscope system.

When the photo interrupter 55 detects that the treatment tool 200 has been inserted through the channel 35, the alert calculation unit 68 of the alert part 73 alerts the user by displaying a display (an alert) R8 on the information display region R7 of the liquid crystal panel 81 of the display unit 80 using text as shown in FIG. 4 when the out-of-viewing-range state calculation unit 67 detects the out-of-viewing state.

Display in the information display region R7 is preferably performed before the treatment tool 200 protrudes from the opening 35a of the distal end side of the channel 35. For this reason, the photo interrupter 55 is preferably attached to a portion as close as possible to the proximal end side of the channel 35.

The user cheeks the display R8 of the information display region R7 of the liquid crystal panel 81, realizes that the treatment tool 200 is not displayed within a visual field even though the user has inserted the treatment tool 200, and therefore stops the insertion of the treatment tool 200 through the channel 35. As shown in FIG. 1, the arm bending part 32 is bent to the first side X1 by manipulating the auxiliary manipulation part 70. When the arm bending part 32 is bent to be in the in-viewing-range state, the out-of-viewing-range state calculation unit 67 transmits a detection result that the arm bending part 32 has been in the in-viewing-range state to the alert calculation unit 68.

The alert calculation unit 68 stops the display R8 of the information display region R7 of the liquid crystal panel 81.

Figure 5:
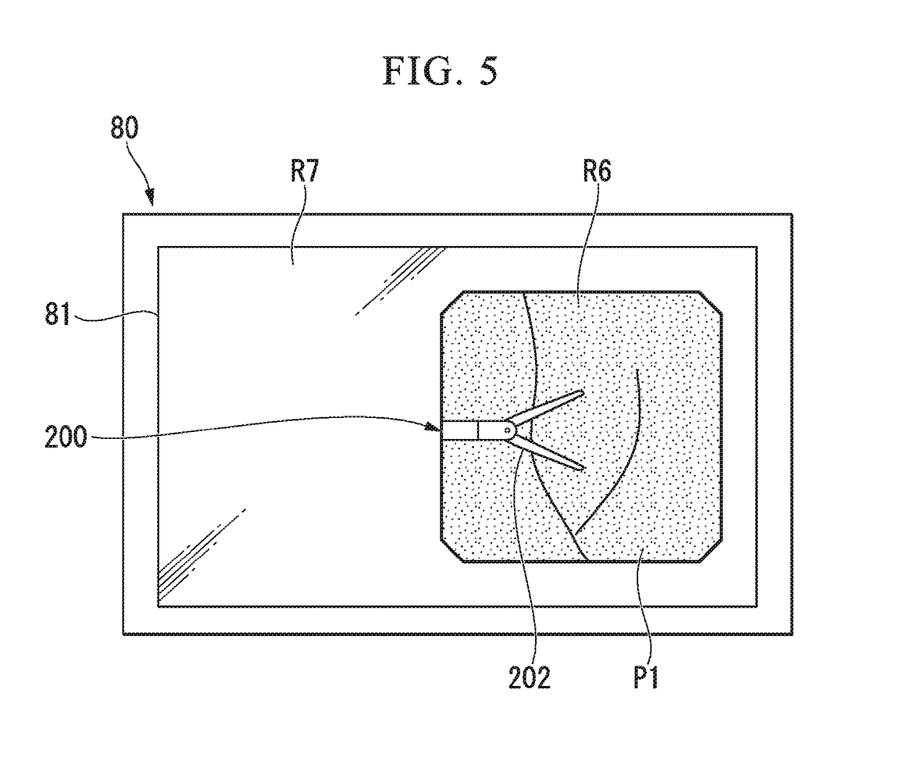
FIG. 5 is a view showing a state in which a grasping part is displayed on an image display region in the display unit.

The user inserts the treatment tool 200 through the channel 35 again and causes the grasping part 202 to protrude from the distal end of the channel 35. The grasping part 202 of the treatment tool 200 which protrudes from the distal end of the channel 35 is observed using the observation unit 20, and as shown in FIG. 5, the grasping part 202 is displayed in the image display region R6 of the display unit 80.

The user understands that the grasping part 202 protrudes from the channel 35 because the grasping part 202 is displayed in the image display region R6. When the treatment tool 200 protrudes by a predetermined amount from the channel 35, the user stops insertion of the treatment tool 200.

The pair of grasping pieces 202a are opened and closed by manipulating the treatment tool manipulation part 203 of the treatment tool 200, and appropriate treatment is thus performed on the site to be treated P1.

As described above, according to the endoscope system according to this embodiment, when the photo interrupter 55 detects that the treatment tool 200 has been inserted through the channel 35, if the first detection part 72 detects that the arm part 30 is in the out-of-viewing-range state, the alert part 73 can alert the user. Therefore, even if the treatment tool 200 protrudes from the channel 35, the treatment tool 200 is suppressed from being continuously inserted. Thus, time efficiency of a procedure can be improved.

The alert part 73 performs an alert by displaying the display R8 in the information display region R7 of the liquid crystal panel 81. Thus, the user can reliably check the content of the alert.

Note that, in this embodiment, although the display R8 using text is given in the information display region R7 of the liquid crystal panel 81, a figure configured to call the user's attention to the alert may be displayed or the text or the figure may blink.

A sound production part such as a speaker may be provided in the alert part instead of the display unit 80 of the alert part 73. In this case, an alert is given to the user by producing a sound from the sound production part.

Although the second detection part is set as the photo interrupter 55, the second detection part may be a metal sensor (a proximity sensor) configured to detect a metal. This is because, in general, a treatment tool is formed of a metal. The metal sensor detects a metal using, for example, a method of using an eddy current which is generated in the metal, a method of detecting a change in electrical capacitance due to approaching of the metal, or the like.

Second Embodiment

Next, a second embodiment of the present invention will be described with reference to FIGS. 6 and 7. The same sites as those of the above-described embodiment are denoted with the same reference numerals, the descriptions thereof will be omitted, and only differences will be described.

Figure 6:
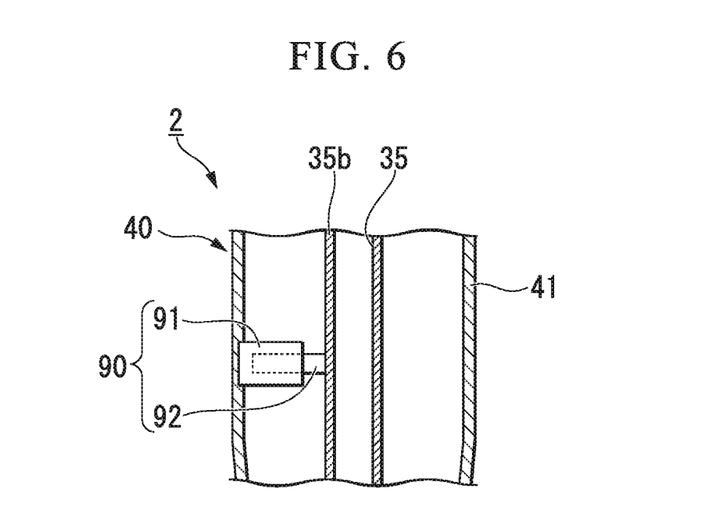
FIG. 6 is a cross-sectional view of a major part of an endoscope system according to a second embodiment of the present invention.
Figure 7:
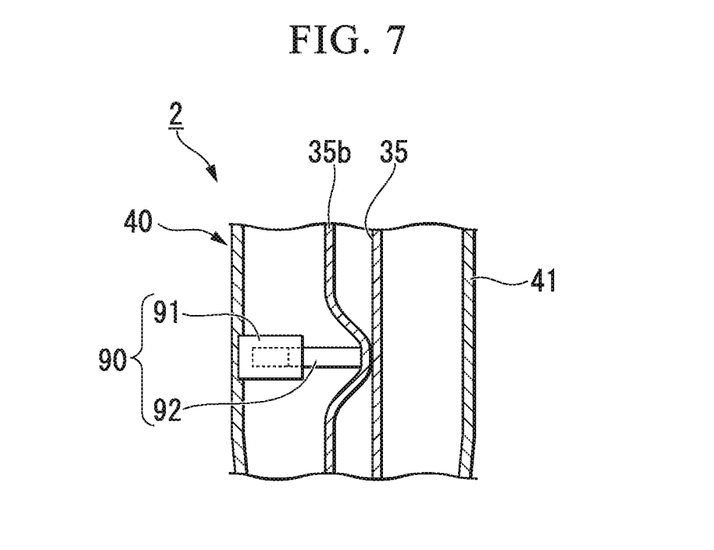
FIG. 7 is a cross-sectional view showing an action of the endoscope system.

As shown in FIG. 6, in an endoscope system 2 according to this embodiment, a blockade part 90 is built in a manipulation part main body 41 of an endoscope manipulation part 40 in addition to the constitutions of the endoscope system 1 according to the first embodiment. The blockade part 90 is configured such that a rod-shaped plunger (an iron core) 92 is inserted through a bottomed cylindrical solenoid 91.

Both ends of a coil (not shown) which is built in the solenoid 91 are connected to a power supply source. The power supply source is connected to a bus 66.

When the coil is not supplied with power, the plunger 92 is retracted to the solenoid 91 side. Here, a channel tube 35b which forms a channel 35 is not crushed, and an inner diameter of the channel 35 is substantially constant regardless of a position of the channel 35 in a longitudinal direction. A distal end portion (an end portion which is opposite to the solenoid 91) of the plunger 92 comes into contact with an outer surface of the channel tube 35b.

In the endoscope system 2 configured in this way, when a photo interrupter 55 detects that a treatment tool 200 has been inserted through the channel 35, if an out-of-viewing-range state calculation unit 67 of a first detection part 72 detects an out-of-viewing-range state, an alert part 73 displays a display R8 to give an alert, and the blockade part 90 performs an action to be described below.

That is to say, a main controller 69 supplies the coil of the solenoid 91 with power through the power supply source. As shown in FIG. 7, the plunger 92 is pushed to the channel tube 35b side by a magnetic field which is generated by the coil, and thus the channel 35 is deformed and a portion of the channel 35 which is pushed by the plunger 92 is crushed. The channel 35 is crushed so that an inside of the channel 35 is blocked, and the treatment tool 200 thus cannot be inserted through the channel 35.

Note that, when supply of power through the power supply source is stopped, the plunger 92 is retracted to the solenoid 91 side. The channel tube 35b of which an inner diameter is reduced by the plunger 92 is returned to an original shape by an elastic force of the channel tube 35b, and the inner diameter of the channel 35 is increased.

As described above, according to the endoscope system 2 according to this embodiment, if an arm part 30 is in an out-of-viewing-range state, when the treatment tool 200 is inserted through the channel 35, an alert can be given to the user.

Also, the blockade part 90 is provided so that the treatment tool 200 can be reliably prevented from being inserted through the channel 35.

Note that, in this embodiment, the channel 35 may be crushed by the blockade part 90 in advance before the treatment tool 200 is inserted through the channel 35. In this case, when the first detection part 72 detects the in-viewing-range state, the blockade part 90 stops crushing the channel 35 and causes the inner diameter of the channel 35 to be returned to an original inner diameter.

Although the blockade part 90 is configured to include the solenoid 91 and the plunger 92, a blockade part is not limited thereto as long as the blockade part is configured to deform at least a portion of the channel 35 such that the treatment tool 200 cannot be inserted through the channel 35.

Third Embodiment

Next, a third embodiment of the present invention will be described with reference to FIGS. 8 to 12. The same sites as those of the above-described embodiments are denoted with the same reference numerals, the descriptions thereof will be omitted, and only differences will be described.

Figure 8:
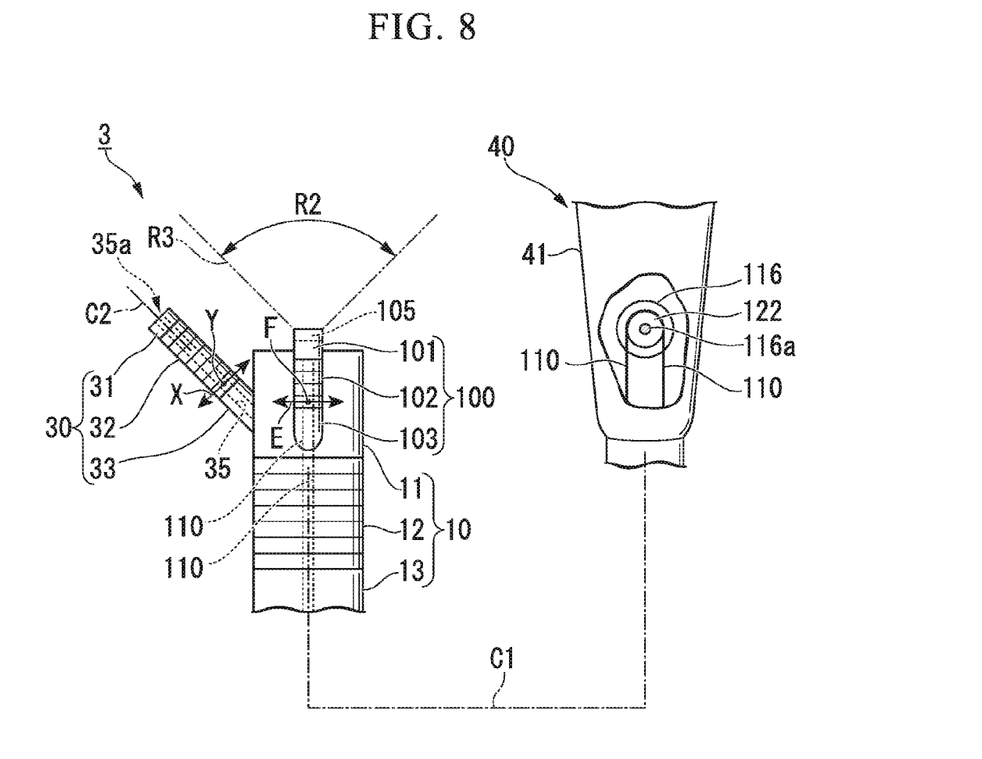
FIG. 8 is a view showing a partly cut major part of an endoscope system according to a third embodiment of the present invention.
Figure 9:
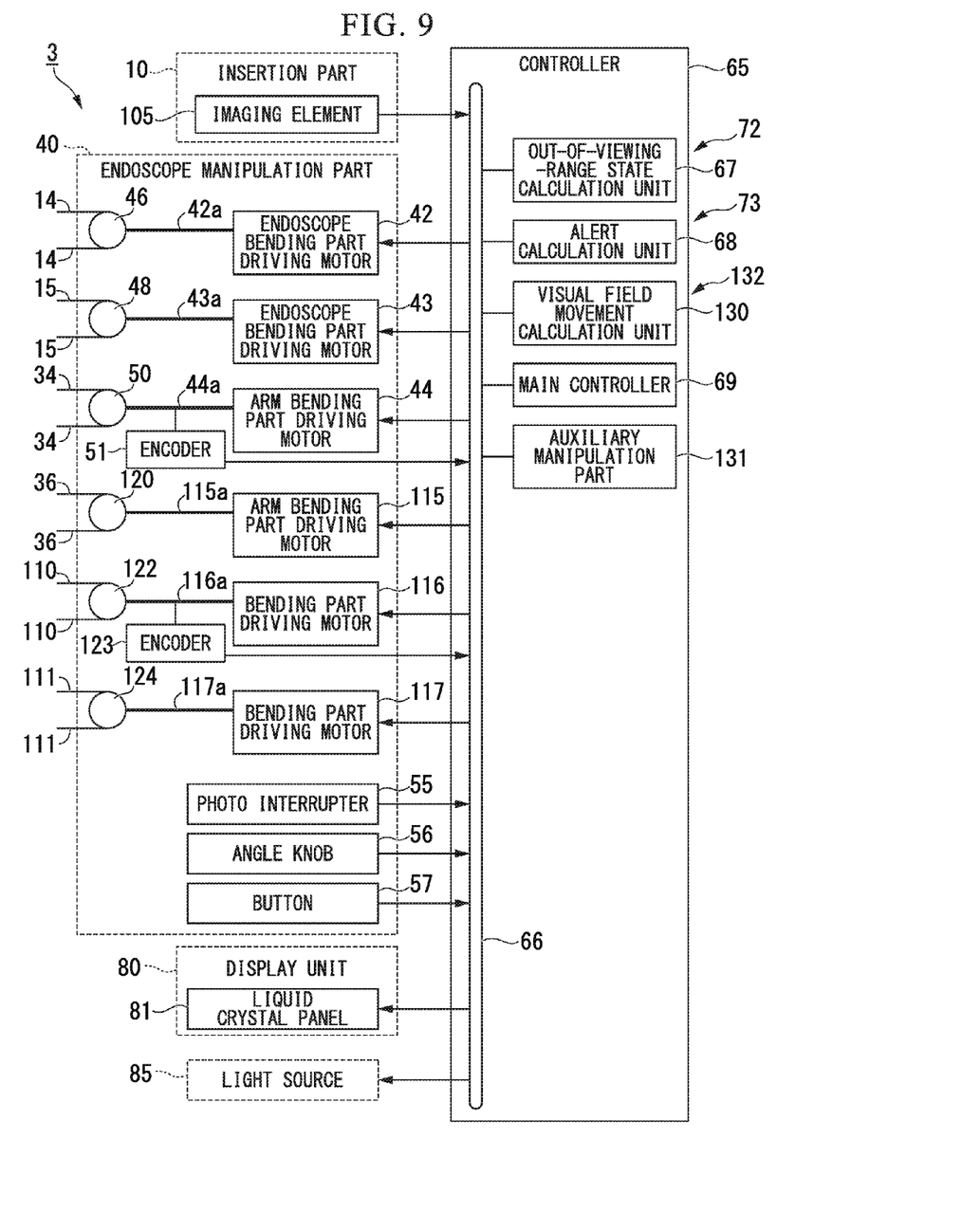
FIG. 9 is a block diagram of the endoscope system.

As shown in FIGS. 8 and 9, an endoscope system 3 according to this embodiment includes an observation unit 100, a visual field movement calculation unit 130, and an auxiliary manipulation part 131 instead of the observation unit 20 and the auxiliary manipulation part 70 of the endoscope system 1 according to the first embodiment.

The observation unit 100 has a rigid rigid part 101 which is provided at a distal end side, a bending part 102 which is provided at a proximal end side of the rigid part 101 and can be manipulated to be bent, and a rigid rigid part 103 which is provided at a proximal end side of the bending part 102.

An imaging element 105 is built in the rigid part 101. The imaging element 105 can observe an inside of a viewing range R2 which is defined in the front of the rigid part 101. The imaging element 105 is connected to a bus 66.

The bending part 102 is configured in the same manner as an arm bending part 32. Distal end portions of two manipulation wires 110 and distal end portions of two manipulation wires 111 are attached to a joint ring (not shown) which is disposed inside the bending part 102 (the manipulation wires 111 are shown only in FIG. 9). The manipulation wires 110 and 111 extend to an endoscope manipulation part 40 through the plurality of joint rings, the rigid part 103, and an insertion part 10.

A proximal end portion of the rigid part 103 is attached to a lateral surface of a distal end rigid part 11.

In this embodiment, distal end portions of two arm manipulation wires 36 are attached to the joint ring (not shown) of an arm part 30 in addition to two arm manipulation wires 34. The arm manipulation wires 34 and 36 are attached around a longitudinal axis of the arm part 30 at equal angles.

An arm bending part driving motor 115 and bending part driving motors 116 and 117 are built in a manipulation part main body 41 of the endoscope manipulation part 40 in addition to the endoscope bending part driving motors 42 and 43 and the arm bending part driving motor 44 according to the first embodiment.

The arm bending part driving motor 115 and the bending part driving motors 116 and 117 are configured in the same manner as the arm bending part driving motor 44. That is to say, a pulley 120 is attached to a rotation shaft 115a of the arm bending part driving motor 115 coaxially with the rotation shaft 115a. Proximal end portions of the two arm manipulation wires 36 are each attached to the pulley 120.

A pulley 122 is attached to a rotation shaft 116a of the bending part driving motor 116 coaxially with the rotation shaft 116a. Proximal end portions of the two manipulation wires 110 are each attached to the pulley 122. An encoder 123 is connected to the rotation shaft 116a of the bending part driving motor 116. The amount of rotation of the rotation shaft 116a and the direction in which the rotation shaft 116a is rotated, which are detected by the encoder 123, are transmitted to a controller 65. Note that a visual field movement unit 132 is constituted by the bending part driving motor 116, the encoder 123, and the visual field movement calculation unit 130.

A pulley 124 is attached to a rotation shaft 117a of the bending part driving motor 117 coaxially with the rotation shaft 117a. Proximal end portions of the two manipulation wires 111 are each attached to the pulley 124.

When the bending part 102 has a straight shape, the rotation shaft 116a of the bending part driving motor 116 is at a reference position.

The arm bending part 32 is bent in a direction Y which is perpendicular to a longitudinal direction of the arm part 30 and a direction X by driving the arm bending part driving motor 115. Note that the direction Y is parallel to one lateral surface R3 in the quadrangular pyramid-shaped viewing range R2. For this reason, even if the arm bending part 32 is bent in the direction Y, the distance between the arm part 30 and the viewing range R2 is not changed.

Note that, a range in which the arm bending part 32 is bent in the direction Y may be limited such that a center axis line C2 in an opening 35a of a channel 35 is not prevented from easily passing through the viewing range R2 of the observation unit 100 when the thin bending part 32 is bent in the direction Y.

The bending part 102 is bent in a direction E which is perpendicular to a longitudinal direction of the observation unit 100 by driving the bending part driving motor 116. A reference surface in which the rigid part 101 is moved when the bending part 102 of the observation unit 100 is bent in the direction E is parallel to a reference surface in which the arm rigid part 31 is moved when the arm bending part 32 of the arm part 30 is bent in the direction X.

On the other hand, the bending part 102 is bent in a direction F which is perpendicular to the longitudinal direction of the observation unit 100 and the direction E by driving the bending part driving motor 117.

The visual field movement calculation unit 130 and the auxiliary manipulation part 131, which were described above, are connected to the bus 66 of the controller 65.

The visual field movement calculation unit 130 is constituted by a calculation element, a memory, a control program, and the like.

The memory of the visual field movement calculation unit 130 stores a table which indicates a direction and an amount of rotation in which a rotation shaft 44a of the arm bending part driving motor 44 is rotated from a reference position and ranges of a direction and an amount of rotation in which the rotation shaft 116a of the bending part driving motor 116 is rotated from the reference position such that the viewing range R2 of the observation unit 100 passes through the center axis line C2 of the arm part 30 with respect to a current bending shape of the arm bending part 32 and the arm bending part 32 is in an in-viewing-range state.

In this embodiment, even if the bending part 102 of the observation unit 100 is bent in the direction F, the in-viewing-range state and an out-of-viewing-range state are not switched. For this reason, an encoder is not attached to the rotation shaft 117a of the bending part driving motor 117 configured to bend the bending part 102 in the direction F, and is attached to the rotation shaft 116a of the bending part driving motor 116 configured to bend the bending part 102 in the direction E.

Figure 10:
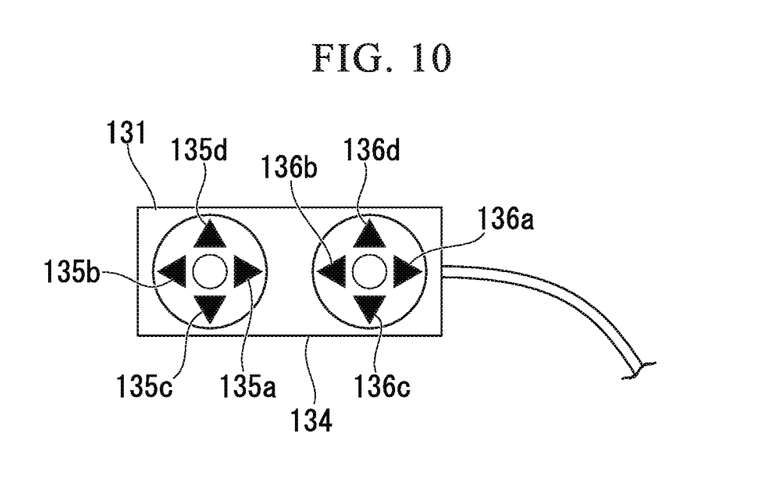
FIG. 10 is a plan view of an auxiliary manipulation part of the endoscope system.

As shown in FIG. 10, in the auxiliary manipulation part 131, bending manipulation buttons 135a to 135d and 136a to 136d are provided on a manipulation part main body 134.

When the bending manipulation buttons 135a and 135b are manipulated, the arm bending part driving motor 44 is driven so that the arm, bending part 32 is bent in the direction X. When the bending manipulation buttons 135c and 135d are manipulated, the arm bending part driving motor 115 is driven so that the arm bending part 32 is bent in the direction Y.

When the bending manipulation buttons 136a and 136b are manipulated, the bending part driving motor 116 is driven so that the bending part 102 is bent in the direction E. Also, when the bending manipulation buttons 136c and 136d are manipulated, the bending part driving motor 117 is driven so that the bending part 102 is bent in the direction F.

Next, an action of the endoscope system 3 configured as described above will be described.

Even in this embodiment, when a photo interrupter 55 detects that a treatment tool 200 has been inserted through the channel 35, if a first detection part 72 detects the out-of-viewing-range state, an alert part 73 alerts the user.

When an out-of-viewing-range state calculation unit 67 of the first detection part 72 detects that the arm bending part 32 is in the out-of-viewing-range state, the calculation element of the visual field movement calculation unit 130 performs an action to be described below. That is to say, the direction and the amount of rotation by which the rotation shaft 116a of the bending part driving motor 116 should rotate from the reference position in order to fall in the in-viewing-range state are calculated on the basis of a direction and an amount of rotation by which the rotation shaft 44a of the arm bending part driving motor 44 has rotated from the reference position and the table which is stored in the memory. Here, the direction and the amount of rotation by which the rotation shaft 116a should rotate are preferably calculated such that an amount of movement from the direction and the amount of rotation in which the rotation shaft 116a has currently rotated from the reference position is reduced.

Figure 11:
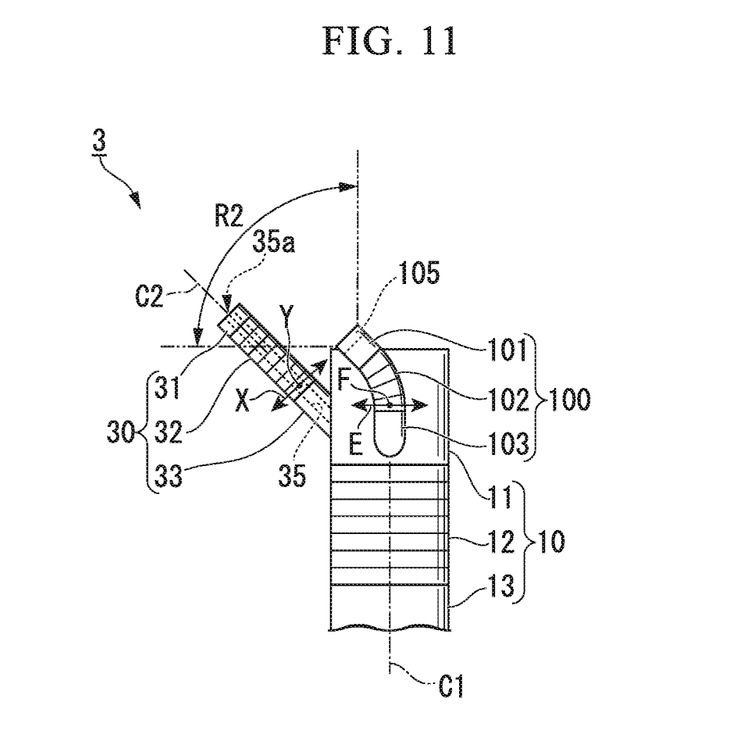
FIG. 11 is a view showing an action of the endoscope system.

The visual field movement calculation unit 130 drives the bending part driving motor 116 on the basis of a calculation result, and as shown in FIG. 11, the observation unit 100 is moved by bending the bending part 102 in the direction E. Thus, the in-viewing-range state in which the center axis line C2 in the opening 35a of the channel 35 passes through the viewing range R2 is achieved.

As described above, according to the endoscope system 3 according to this embodiment, if the arm part 30 is in the out-of-viewing-range state, the user can be alerted when the treatment tool 200 is inserted through the channel 35.

Also, the visual field movement unit 132 is provided so that the observation unit 100 is moved without bending the arm bending part 32 of the arm part 30. Thus, the in-viewing-range state is achieved.

Note that, in this embodiment, the bending part 102 which can be manipulated to be bent is provided in the observation unit 100. However, like an endoscope system 3A shown in FIG. 12, an observation unit 140 may be formed of a hard material. In this modified example, a distal end surface 11a of a distal end rigid part 11 is formed with a recessed part 11b.

Figure 12:
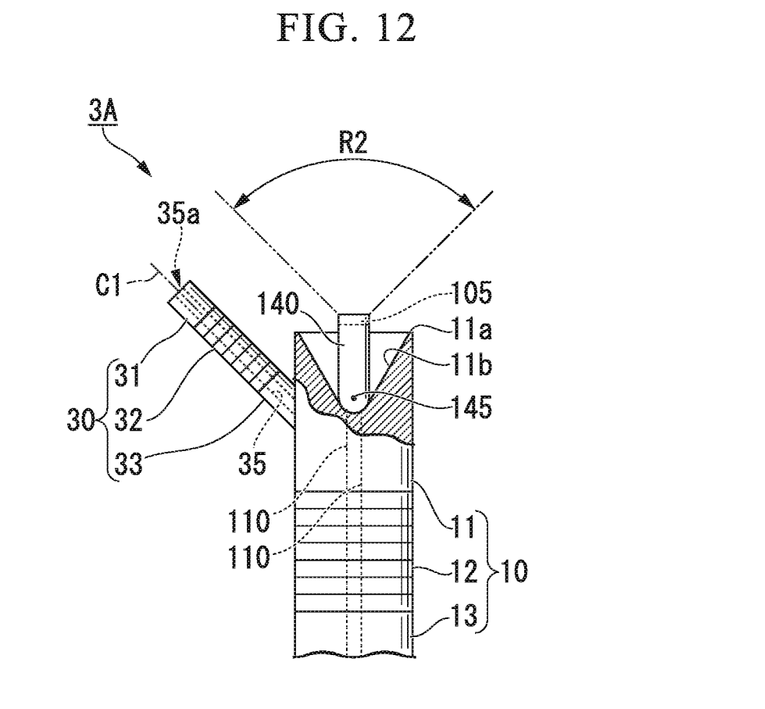
FIG. 12 is a view showing a partly cut endoscope system in a modified example of the third embodiment of the present invention.

The observation unit 140 is disposed inside the recessed part 11b of the distal end rigid part 11, and a proximal end portion of the observation unit 140 is rotatably supported by a pin 145 at the distal end rigid part 11. Distal end portions of the two manipulation wires 110 are attached to the proximal end portion of the observation unit 140. The observation unit 140 can be rotated around the pin 145 by driving the bending part driving motor 116.

The first embodiment to the third embodiment of the present invention have been described in detail above with reference to the drawings, but a specific constitution is not limited to the embodiments, and changes, combinations, deletions, and the like of the constitutions are included without departing from the scope of the present invention. In addition, it should be noted that the constitutions illustrated in the embodiments can be appropriately combined and used.

For example, in the first embodiment to the third embodiment, the proximal end portion of the arm part 30 is attached to the lateral surface of the distal end rigid part 11. However, the proximal end portion of the arm part 30 may be attached to the distal end surface 11a of the distal end rigid part 11. Since an observation unit is in an out-of-viewing-range state when a viewing range of the observation unit is relatively narrow in many cases, an endoscope system according to this embodiment can be appropriately used.

The opening 35a of the channel 35 is formed on the distal end surface of the arm rigid part 31. However, a position at which the opening 35a is formed is not particularly as long as the position is at the arm rigid part 31.

When the endoscope bending part driving motors 42 and 43 are not provided in the endoscope system, endoscope manipulation wires 14 and 15 may be directly connected to an angle knob 56. Even in this case, the endoscope manipulation wires 14 and 15 are advanced or retracted by manipulating the angle knob 56 so that the endoscope bending part 12 is bent.

An overtube and an endoscope may be provided in the endoscope system, and the insertion part 10 may be constituted by the overtube and an endoscope insertion part of they endoscope which is inserted through the overtube. In this case, an arm part is attached to the overtube.

What is claimed is:

1. An endoscope system comprising:
   an insertion part capable of being inserted into a body;
   an observation part provided at the insertion part, the observation part being capable of observing an inside of a viewing range defined in a front of the observation part;
   an arm part capable of being manipulated to be bent, a proximal end portion of the arm part being provided at the insertion part, the arm part having an opening of a channel, through which a treatment tool is capable of being inserted, provided at a distal end side of the arm part;
   a first detection part that detects an out-of-viewing-range state in which a center axis line in the opening of the channel does not pass through the viewing range of the observation part;
   a second detection part that detects that the treatment tool has been inserted through the channel;
   an alert part that alerts a user when the second detection part detects that the treatment tool has been inserted through the channel and the first detection part detects the out-of-viewing-range state; and
   a blockade part configured to deform at least a portion of the channel such that the treatment tool is incapable of being inserted through the channel if the first detection part detects the out-of-viewing-range state when the second detection part detects that the treatment tool has been inserted through the channel.

2. The endoscope system according to claim 1, further comprising:
   a visual field movement unit that moves the observation part such that the center axis line in the opening of the channel passes through the viewing range if the first detection part detects the out-of-viewing-range state when the second detection part detects that the treatment tool has been inserted through the channel.

3. The endoscope system according to claim 1, wherein the alert part displays an alert or generates a sound.

4. A method of operating an endoscope system, the endoscope system including an insertion section capable of being inserted into a body, one or more lenses provided at the insertion section, the one or more lenses being configured to observe an inside of a viewing range defined in a front of the one or more lenses, an arm capable of being manipulated to be bent, a proximal end portion of the arm being provided at the insertion section, the arm having an opening of a channel configured to accept a treatment tool inserted therein, the channel being provided at a distal end side of the arm, a rotation shaft configured to generate a driving force to bend the arm by rotation of the rotation shaft, a first sensor configured to detect an amount of rotation of the rotation shaft; a second sensor configured to detect an insertion of the treatment tool into the channel of the arm, and a controller configured to alert a user, the method comprising:

detecting an out-of-viewing-range state in which a center axis line in the opening of the channel passes a position out of the viewing range of the one or more lenses based on the amount of rotation of the rotation shaft detected by the first sensor;

detecting that the treatment tool has been inserted through the channel by the second sensor; and     alerting the user when that the treatment tool is detected as being inserted through the channel and the out-of-viewing-range state is detected.

5. An endoscope system comprising:

an insertion section inserted into a body, the insertion section having one or more lenses configured to observe an inside of the body;

an arm having an opening of a channel configured to accept a treatment tool inserted therein, a direction in which the opening faces is changed by bending of the arm;

a rotation shaft configured to generate a driving force to bend the arm by rotation of the rotation shaft;

a first sensor configured to detect an amount of rotation of the rotation shaft;

a second sensor configured to detect an insertion of the treatment tool into the channel of arm; and     a controller configured to;

detect an out-of-viewing-range state in which a center axis line in the opening passes a position out of a viewing range of the one or more lenses based on the amount of rotation of the rotation shaft detected by the first sensor; and         alert a user when the second sensor detects an insertion of the treatment tool into the channel of the arm and the controller detects the out-of-viewing-range state.

6. The endoscope system according to claim 5, wherein the controller is further configured to block at least a portion of the channel such that the treatment tool is incapable of being inserted through the channel when the out-of-viewing-range state is detected and the treatment tool is detected as being inserted through the channel.

7. The endoscope system according to claim 5, wherein the controller is further configured to move the one or more lenses such that the center axis line in the opening of the channel passes through the viewing range when the out-of-viewing-range state is detected and the treatment tool is detected as being inserted through the channel.

8. The endoscope system according to claim 5, wherein the alert comprises one of displaying an alert or generating a sound.

* * * * *